(12) United States Patent
Cook et al.

US009468674B2

(10) Patent No.: US 9,468,674 B2
(45) Date of Patent: *Oct. 18, 2016

(54) METHODS OF USE OF SECRETORY IGA

(71) Applicant: WISCONSIN ALUMNI RESEARCH FOUNDATION, Madison, WI (US)

(72) Inventors: Mark E. Cook, Madison, WI (US); Jordan Marshall Sand, Madison, WI (US); Lisa Ann Krugner-Higby, Belleville, WI (US); James Mukasa Ntambi, Fitchburg, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 142 days.

This patent is subject to a terminal disclaimer.

(21) Appl. No.: 14/034,633

(22) Filed: Sep. 24, 2013

(65) Prior Publication Data
US 2015/0086534 A1 Mar. 26, 2015

(51) Int. Cl.
*A61K 39/395* (2006.01)
*C07K 16/00* (2006.01)
*A61K 39/00* (2006.01)

(52) U.S. Cl.
CPC ............ *A61K 39/395* (2013.01); *C07K 16/00* (2013.01); *A61K 2039/505* (2013.01); *C07K 2317/10* (2013.01); *C07K 2317/52* (2013.01)

(58) Field of Classification Search
None
See application file for complete search history.

(56) References Cited

U.S. PATENT DOCUMENTS

| 3,658,551 | A | 4/1972 | Bundus et al. |
| 5,258,177 | A | 11/1993 | Uemura et al. |
| 5,607,840 | A | 3/1997 | Van Gorp et al. |
| 2001/0049119 | A1 | 12/2001 | Lee et al. |
| 2008/0145371 | A1* | 6/2008 | Simon .................. A61K 31/415 424/176.1 |
| 2008/0145420 | A1 | 6/2008 | Simon |
| 2011/0305753 | A1 | 12/2011 | Simon |
| 2012/0045517 | A1* | 2/2012 | Simon .................. C07K 16/065 424/499 |
| 2014/0193395 | A1 | 7/2014 | Sand et al. |

FOREIGN PATENT DOCUMENTS

| EP | 0479597 A2 | 4/1992 | |
| EP | 2138186 A1 | 12/2009 | |
| WO | 02063948 A2 | 8/2002 | |
| WO | 2004000035 A1 | 12/2003 | |
| WO | 2009156301 A1 | 12/2009 | |
| WO | 2012080306 A1 | 6/2012 | |
| WO | 2013087911 A1 | 6/2013 | |
| WO | WO 2013087911 A1 * | 6/2013 | ........... C07K 16/241 |
| WO | 2013132052 A1 | 9/2013 | |
| WO | 2014107269 A1 | 7/2014 | |

OTHER PUBLICATIONS

Ananthakrishnan et al., Inflamm Bowel Dis. Aug. 2013;19(9):2021-30. doi: 10.1097/MIB.0b013e318281f5c5.*
Wold et al., Adv Exp Med Biol. 2000;478:77-93.*
Kull et al., Journal of Allergy and Clinical Immunology vol. 116, Issue 3, Sep. 2005, pp. 657-661.*
Mantis et al., Mucosal Immunol. Nov. 2011;4(6):603-11. doi: 10.1038/mi.2011.41. Epub Oct. 5, 2011.*
Janeway et al., Immunobiology, $3^{rd}$ edition, 1997, Garlang Publishing Inc., pp. 3:26-3:31 and 8:19-8:21.*
Pasquier et al., APMIS. May 1992;100(5):383-92.*
Eason et al., Semin Immunol. Aug. 2004;16(4):215-26.*
Yano et al., Appl Environ Microbiol. Dec. 1995;61(12):4480-3.*
Ringo et al., J Appl Microbiol. Jan. 1999;86(1):22-8.*
van Borm et al., Proc Biol Sci. Oct. 7, 2002;269(1504):2023-7.*
Berlanga et al., Int Microbiol. Dec. 2009;12(4):227-36.*
Husseneder et al., PLoS One. Aug. 20, 2014;9(8):e105582. doi: 10.1371/journal.pone.0105582. eCollection 2014.*
Antuofermo et al., BMC Vet Res. Jan. 14, 2014;10:18. doi: 10.1186/1746-6148-10-18.*
Campbell et al., PLoS One. Mar. 8, 2016;11(3):e0150502. doi: 10.1371/journal.pone.0150502. eCollection 2016.*
Merriam Webster's Collegiate Dictionary, $10_{th}$ edition, 1993, definition of "incidence", p. 587.*
Bourne et al.; "Intestinal Immunoglobulins in the Pig"; Biochim. Biophys. Acta; 229; pp. 18-25; (1971).
Porter et al.; "Intestinal Secretion of Immunoglobulins and Antibodies to *Escherichia coli* in the Pig"; Immunology; 18; pp. 909-920; (1970).
Yao et al.; "Isolation and Purification of Bovine Colostrum sIgA and IgG"; Journal of Northeast Agricultural University; 15(1); pp. 58-61; (2008).
Balan et al.; "Orally Administered Ovine Serum Immunoglobulins Influence Growth Performance, Organ Weights, and Gut Morphology in Growing Rats"; Journal of Nutrition; 139(2); pp. 244-249; (2008).
Boullier et al; "Secretory IgA-Mediated Neutralization of Shigella flexneri Prevents Intestinal Tissue Destruction by Down-Regulating Inflammatory Circuits"; Journal of Immunology; 183(9); pp. 5879-5885; (2009).
Kanamaru, et al.; "Some Properties of Secretory IgA Purified from Bovine Colostrum"; Agric. Biol. Chem.; 46(8); pp. 2009-2014; (1982).
Kim et al.; "Optimal Dietary Ratio of Spray Dried Plasma Protein (DSPP) and Dried Porcine Solubles (DPS) in Improving Growth Performance and Immune Status in Pigs Weaned at 21 Days of Age"; Asian-Aust. Journal of Animal Sciences; 14(3); pp. 338-345; (2001).
Mantis et al; "Secretory IgA's Complex Roles in Immunity and Muscosal Homeostasis in the Gut"; Mucosal Immunology; 4(6); pp. 60-611; (2011).

(Continued)

Primary Examiner — Michael Szperka
(74) *Attorney, Agent, or Firm* — Cantor Colburn LLP

(57) ABSTRACT

Described herein are methods of preventing and/or treating inflammation in a barrier surface structure in an individual in need thereof by orally administering to the individual an anti-inflammatory amount of secretory IgA.

22 Claims, 3 Drawing Sheets

(56) References Cited

OTHER PUBLICATIONS

RU2005109538 (A); published Sep. 10, 2006; English Abstract only; 3 pages.
Cerutti et al.; "Regulation of Mucosal IgA Responses: Lessons from Primary Immunodeficiencies"; Ann. N.Y. Acad. Sci.; 1238; pp. 132-144; (2011).
Inoue et al.; "Oral Treatment with Probiotic Lactobacillus Johnsonii NCC533 (La1) for Specific Part of the Weaning Period Prevents the Development of Atopic Dermatitis Induced after Maturation in Model Mice, NC/Nga"; British Journal of Dermatology; 156; pp. 499-509; (2007).
Jin, et al.; "Animal Models of Atopic Dermatitis"; J. Invest Dermatol.; 129(I); pp. 31-40; (2009).
Krugner-Higby et al.; "Ulcerative Dermatitis in C57BL/6 Mice Lacking Stearoyl CoA Desaturase 1"; Comparative Medicine; 62(4); pp. 257-263; (2012).
Kukkonen et al.; "High Intestinal IgA Associates with Reduced Risk of IgE-Associated Allergic Diseases"; Pediatr Allergy Immunol; 21; pp. 67-73; (2010).
Lundell, et al.; "High Circulating Immunoglobulin A Levels in Infants are Associated with Intestinal Toxigenic *Staphylococcus aureus* and a Lower Frequency of Exzema"; Clinical & Experimental Allergy; 39; 662-670; (2009).
Luoviksson et al.; "Allergic Diseases and Asthma in Relation to Serum Immunoglobulins and Salivary Immunoglobulin A in Pre-School Children: a Follow-Up Community-Based Study"; Clin Exp Allergy; 35; pp. 64-69; (2005).
Marschan et al.; "Probiotics in Infancy Induce Protective Immune Profiles That Are Characteristic for Chronic Low-Grade Inflammation"; Clinical and Experimental Allergy; 38; pp. 611-618; (2008).
Marsella et al.; "Investigation of the Effect of Probiotic Exposure on Filaggrin Expression in an Experimental Model of Canine Atopic Dermatitis"; Vet Dermatol; 24; pp. 260-e57; (2013).
Tengvall et al.; "Genome-Wide Analysis in German Shepherd Dogs Reveals Association of a Locus on CFA 27 with Atopic Dermatitis"; PLOS Genetics; 9(5); e1003475; pp. 1-12; www.plosgenetics.org; (2013).
Yel, Leman; "Selective IgA Deficiency"; J. Clin Immunol; 30; pp. 10-16; (2010).
Ferm-O-Tide XP, Products Information Sheet by Midwest AG Enterprises; http://midwestagenterprises.com/ferm-o-tideXP.tml; printed Jan. 22, 2013; 1 page.
Mestecky et al.; "Intestinal IgA: Novel Views on its Function in the Defence of the Largest Mucosal Surface"; Gut; 44; pp. 2-5; (1999).
Pierce et al.; "Effects of Spray-Dried Animal Plasma and Immunoglobulins on Performance of Early Weaned Pigs"; Journal of Animal Science; 83; pp. 2876-2885; (2005).
U.S. Appl. No. 13/734,426, filed Jan. 4, 2013; "Secretory IGA Compositions, Methods of Making and Methods of use Thereof".
Hofmann, Michael; High Quality Supplementary Feed Line with Colostrum: LR Brings Professional on the Animal Market (With Picture); na Presseportal; pp. 1-3; (2011); http://www.presseportal.de/pm/76151/2034045; google translation.
Bodammer et al.; "Alteration of DSS-mediated Immune Cell Redistribution in Murine Colitis by Oral Colostral Immunoglobulin"; BMC Immunology, 14(1); p. 10 (2013).
International Search Report and Written Opinion; International Application No. PCT/US2013/073807; International Filing Date Dec. 9, 2013; Date of Mailing Apr. 10, 2014; 23 pages.
Ahmadi et al.; "Benefits of Bovine Colostrum in Nutraceutical Products"; Journal of Agroalimentary Processes and Technologies; 17(1), pp. 42-45, (2011).

\* cited by examiner

METHODS OF USE OF SECRETORY IGA

FIELD OF THE DISCLOSURE

The present disclosure is related to methods of use of secretory IgA to treat certain inflammatory conditions in humans and animals, particularly dermatitis, including atopic and ulcerative dermatitis.

BACKGROUND

Dermatitis is a general term that describes an inflammation of the skin. Atopic dermatitis, for example, is a pruritic inflammatory skin disorder that affects human children and adults, as well as animals. It is believed that in atopic dermatitis, exposure to irritants and allergens involves both immunological and inflammatory pathways, resulting in skin lesions and pruritus. In humans, atopic dermatitis is sometimes called atopic eczema. Atopic dermatitis in infants, also called infantile eczema, causes an increase in the tendency to develop asthma and allergic reaction later in life, a progression called the atopic march. Early and effective treatment of atopic dermatitis in infants could result in a reduction in problems later in life.

In dogs, atopic dermatitis also presents as pruritus, evidenced by scratching, and chewing, rubbing, or licking the face and feet. Hot spots in dogs, also known as moist dermatitis, are localized spots of skin inflammation that are a source of great agitation for dogs, causing the dog to become fixated on the itchy spot, bothering it constantly until a wound develops. Often hot spots become infected and require treatment with antibiotics. Like dogs, cats can also suffer from atopic dermatitis and hot spots.

Ulcerative dermatitis (UD) is a severe form of atopic dermatitis characterized by ulcerative skin lesions. UD has been noted as a problem in laboratory mice, particularly C57BL/6 (B6) background mice, leading to euthanasia of affected animals due to enlargement of the stable ulcer and/or extreme self-trauma to the affected areas. Given the cost of producing specialized strains of laboratory mice, euthanasia of even a single laboratory animal due to UD is an unacceptable outcome.

What is needed are new treatments for chronic inflammatory disorders, such as dermatitis.

BRIEF SUMMARY

In one aspect, a method of preventing and/or treating inflammation in a barrier surface structure in an individual in need thereof comprises orally administering to the individual an anti-inflammatory amount of secretory IgA.

In another aspect, a method of preventing and/or treating ulcerative dermatitis in a C57BL/6 background laboratory mouse comprises orally administering to the C57BL/6 background laboratory mouse an anti-inflammatory amount of secretory IgA.

Also included herein is a dog or cat food additive comprising an excipient and secretory IgA.

DETAILED DESCRIPTION

Figure 1:
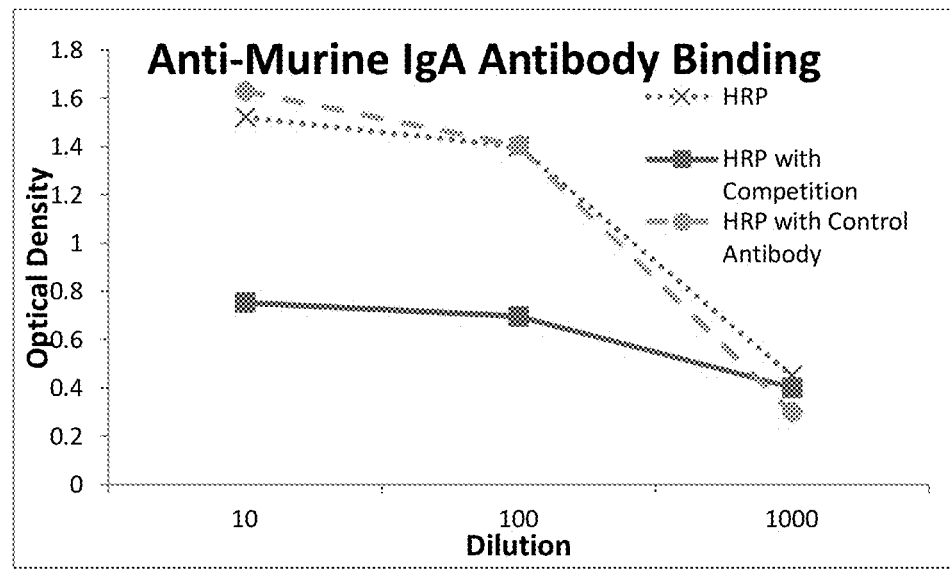
FIG. 1 shows the specificity of created anti-murine IgA egg antibodies using horseradish peroxidase (HRP)-conjugated anti-murine IgA egg antibody in an ELISA. Mouse IgA was attached to plates which were then tested using one of three treatments: 1) HRP-conjugated anti-murine IgA egg antibody only (HRP; dotted line), 2) HRP-conjugated anti-murine IgA egg antibody plus anti-murine IgA egg antibody that was unlabeled (HRP with competition; solid line), and 3) HRP-conjugated anti-murine IgA egg antibody plus unlabeled control nonspecific egg antibody (HRP with control antibody; dashed line). The results demonstrate that the egg antibody is specific for the substrate of murine IgA because it binds the substrate and binding is competed with an unlabeled anti-murine IgA egg antibody but not with a control nonspecific egg antibody.

Secretory IgA (SIgA) is an immunoglobulin with diverse antigen binding activity. When SIgA is released from the intestinal mucosa to the external environment, it forms immune complexes with pathogens and commensal gut flora, food antigens and allergens, thereby preventing them from binding to and penetrating the intestinal mucosa. SIgA acts as an anti-inflammatory molecule by blocking immune cell-antigen interactions. In fact, SIgA deficiency is the most common human immunodeficiency. Reported clinical manifestations of SIgA deficiency in humans include respiratory infections, gastrointestinal disorders, and allergic disorders including atopic dermatitis.

While there has been some suggestion that increased SIgA might be clinically useful, the results thus far have been inconclusive. For example, while increased endogenous levels of SIgA have been correlated to decreased allergic disorders, a number of other biomarkers were also correlated, confounding the results. Further, in a study of probiotic administration in children, increased plasma IgA was measured, however, there was no effect on asthma and allergy. Despite the suggestion that SIgA might have some connection to allergy, there has been no empirical study showing that the concentration of endogenous SIgA in the intestinal tract is linked to skin disorders. Prior to the present invention, it was unknown if orally administered SIgA could be used to treat chronic skin disorders such as ulcerative dermatitis. With regard to dermatitis, it was particularly unknown if orally administered SIgA, which is located in the lumen of the intestine, would effectively bind microbial and/or food antigens related to dermatitis, preventing their leakage into the circulation and interaction with immune cells in the skin. It has been unexpectedly shown by the inventors herein that orally administered SIgA can be used to prevent and reverse ulcerative dermatitis as well as other inflammatory conditions.

Specifically, a mouse model for the induction of dermatitis that leads to ulcerative dermatitis was used to study the effects of secretory IgA on dermatitis. In this model, stearoyl CoA-desaturase global knock-out mice ($SCD^{-/-}$) placed on a semipurified casein-based diet develop nearly 100% dermatitis. In one study, the inventors discovered that feeding purified swine SIgA extracted from the intestinal contents of swine or a dried mucosal preparation containing SIgA to $SCD^{-/-}$ mice on a dermatitis-inducing diet resulted in a reduction in the development of ulcerative dermatitis. The reduction in ulcerative dermatitis was dose-dependent. While 100% of the control mice developed dermatitis, only 50% of the mice fed 0.33 grams and 14% of the mice 1 gram of SIgA/Kg diet developed dermatitis.

In an additional study, mice that had already developed ulcerative dermatitis (a condition that often results in the need for euthanasia of affected mice) were fed 1 gram SIgA (or mucosa containing SIgA, with the same LPS-binding capacity as 1 gram pure SIgA). The symptoms of ulcerative dermatitis were dramatically reduced or eliminated in all four of the treated mice that had ulcerative dermatitis.

As used herein, "barrier surface structures" in an individual are those cells, secretions, and matrices that prevent the translocation of environmental antigens to systemic processes. Barrier surface structures are found in the eye, ear, skin, intestine, airways, reproductive tract, and urinary tract. SIgA is an anti-inflammatory immunoglobulin secreted from these barrier structures to the surface of the environment or into the associated milieu (e.g., intestinal lumen content and urine). Research shows that dysfunction in one barrier surface structure can induce inflammation in another due to antigen translocation and/or immune interaction at another barrier surface structure.

In one aspect, included herein is a method of preventing and/or treating inflammation in a barrier surface structure in an individual in need thereof, comprising orally administering to the individual an anti-inflammatory amount of secretory IgA. The SIgA can be administered directly to the intestinal barrier surface structure thereby protecting the intestinal barrier surface structure or another barrier surface structure (e.g., the skin). The secretory IgA can be orally administered as a pharmaceutical composition or as a food composition.

As used herein, the term individual includes humans and animals, including non-human mammals and non-mammalian species. Exemplary non-human mammals include dogs, cats, mice and rats including laboratory animals, nonhuman primates, pigs, sheep, cattle, and horses. Exemplary non-mammalian species include chickens, turkeys, and ducks that have dermatitis, as well as amphibians and fish with ulcerative skin disease.

As used herein, the term anti-inflammatory amount means an amount of orally administered SIgA that can prevent and/or reduce inflammation of a barrier surface structure in the target species. The term prevent inflammation means to reduce the incidence of at least one symptom of an inflammatory disorder characterized by inflammation of a barrier surface structure in an individual at risk of developing the inflammatory disorder, that is, an individual not evidencing all of the symptoms of the inflammatory disorder at the time of SIgA administration. For example, an individual may evidence scratching without further evidence of inflammatory disorders. Upon SIgA treatment, the individual will exhibit relief from the worst evidence of pruritus (itching) and the worst consequences such as self-trauma and ulcerative dermatitis would be prevented. In one aspect, an animal at risk of developing an inflammatory disorder characterized by inflammation of a barrier surface structure with accompanying pruritus is a C57BL/6 background laboratory mouse, or a dog or cat that is prone to developing hot spots. Because C57BL/6 background laboratory mice and dogs/cats prone to hot spots are known to be extremely susceptible to barrier surface inflammation, treatment of such animals in the absence of visible signs of inflammation may be warranted to prevent future inflammatory flare-ups. The term "treat" or "reduce" inflammation means a visible and/or measurable reduction in at least one symptom of the inflammatory disorder characterized by inflammation of a barrier surface structure. For example, for an individual with ulcerative dermatitis, a reduction in symptoms means a lessening of the severity and/or frequency of ulcerative lesions and/or pruritus.

Anti-inflammatory amounts of secretory IgA can be determined by one of ordinary skill in the art. Exemplary amounts are 0.01 to 25 g/kg food, specifically 1 to 10 g/Kg food or 1 to 1000 mg/Kg body weight.

Inflammatory disorders are conditions that involve inflammation that can affect many barrier surface structures of the body. Inflammatory disorders characterized by inflammation of a barrier surface structure include dermatitis; disorders characterized by gastrointestinal inflammation such as inflammatory bowel disease, ulcerative colitis, Crohn's disease; and lymphocytic or eosinophilic gastroenteritis; ocular inflammatory disorders; and inflammatory airway disorders such as asthma and allergy.

Dermatitis an inflammation of the skin, while chronic dermatitis is persistent dermatitis with symptoms that generally lasts weeks, months or years. Chronic dermatitis includes atopic dermatitis (also called atopic eczema), chronic actinic dermatitis, ulcerative dermatitis, allergic contact dermatitis, irritant contact dermatitis, and psoriasis. In one aspect, the individual with dermatitis suffers from skin lesions that are resistant to healing.

Atopic dermatitis is a pruritic, inflammatory skin disorder that affects human children and adults, as well as animals. Atopic dermatitis leads to scratching, redness, flaky skin, raised bumps, rashes, and open lesions. In humans, atopic dermatitis often appears on the arms, the hands, the feet, the upper chest and behind the knees, although it can appear in other locations. Atopic dermatitis in humans often appears in childhood and persists through adulthood. A serious problem in patients with atopic dermatitis is that scratching the rash can lead to breaking of the skin barrier, allowing for bacterial infections such as *Staphylococcus aureus*. Treatments for atopic dermatitis include topical steroids, topical immunosuppressants (e.g., tacrolimus and similar compounds), antihistamines, and antibiotics to treat infections.

Infantile eczema is a type of atopic dermatitis that occurs in infants. In some cases, infantile eczema continues through childhood, adolescence, and adulthood. Infantile eczema is generally characterized by an itchy dry rash on the face and scalp. Children with infantile eczema have a high sensitivity to itching and have an increased risk of developing other inflammatory conditions such as asthma and allergies.

Atopic dermatitis is also problematic in animals, particularly dogs and cats. Atopic dermatitis usually begins in dogs from 1-3 years of age and, while prevalent in certain breeds, can affect any breed of dog and mixed breed dogs. It is estimated that atopic dermatitis affects 10% of dogs. The disorder is evidenced by itching, licking and face-rubbing, including licking of the paws. "Hot spots" are localized areas of red, moist, hot, irritated skin lesions. Clinically, the lesions appear to be the result of self-trauma. Extreme self-trauma to the affected spot can lead to skin infections, requiring treatment with antibiotics. The current standard treatment for hot spots is oral prednisone, however, many dogs are prednisone-intolerant. In addition, prednisone treatment in dogs can lead to excessive thirst, excessive urination, diarrhea, and weight fluctuations. In one embodiment, the individual is a prednisone-intolerant dog or a dog for which prednisone is contraindicated due to its side effects. In another aspect, the dog is co-administered a medication that is incompatible with steroid administration. For instance, corticosteroid drugs such as prednisone cannot be co-administered with nonsteroidal anti-inflammatory drugs (NSAIDS) such as carprofen or meloxicam because the corticosteroids vastly increase the risk of gastrointestinal bleeding due to the NSAIDS.

Chronic actinic dermatitis, known as photosensitivity dermatitis or actinic reticuloid syndrome (PD/AR), is a condition in which the skin becomes inflamed, particularly in areas that have been exposed to sunlight or artificial light. Chronic actinic dermatitis is generally found in men over the age of 50, but women and younger individuals can also be affected. Diagnosis of chronic actinic dermatitis can be challenging because the wavelengths of light involved do not cause sunburn, so individuals can have problems on cloudy days and through clothing and windows. Topical treatments such as topical steroids are the current treatments for this disorder.

Ulcerative dermatitis is a severe form of atopic dermatitis characterized by ulcerative skin lesions. UD has been noted as a problem in laboratory mice, particularly C57BL/6 (B6) background mice, than can lead to euthanasia of affected animals, due to enlargement of the ulcer or extreme self-trauma to the affected areas. In one aspect, the individual is a laboratory mouse with a C57BL/6 background. In other aspects, the individual is a cat with feline ulcerative dermatitis, a turkey with focal ulcerative dermatitis, a chicken with gangrenous dermatitis, a pig with porcine ulcerative dermatitis, ulcerative dermatitis in reptiles, and fish and frogs such as *Xenopus* frogs.

Both allergic and irritant contact dermatitis are conditions in which the skin becomes red, sore, itchy and/or inflamed after contact with a substance. Allergic contact dermatitis is caused when the skin comes in contact with a substance with which the individual has become particularly sensitive. Exemplary allergens include fabrics or clothing, adhesives, nickel or other metals, poisonous plants and latex. Irritant contact dermatitis is generally caused by contact with soaps and detergents, laundry soaps and softeners, solvents, and other chemicals. Irritant contact dermatitis can look like a burn.

In one aspect, the inflammatory disorder characterized by inflammation of a barrier surface structure is further characterized by chronic gastrointestinal inflammation such as inflammatory bowel disease, ulcerative colitis, and Crohn's disease. Inflammatory bowel disease (IBD) is a general term for chronic inflammation of all or part of the digestive tract. Ulcerative colitis and Crohn's disease are the most common forms of IBD in humans. IBD is also found in pets such as dogs and cats, and farmed animals (e.g., cattle, sheep chickens, turkeys, ducks, fish species and horses), and is generally characterized by diarrhea and/or vomiting. In one aspect, the individual is a dog or a cat with inflammatory bowel disease.

Ulcerative colitis is chronic inflammation of the colon including necrotizing enterocolitis in newborns. Ulcers form where the inflammation has killed the cells that line the colon. Ulcerative colitis can occur in children, but generally begins between ages 15 and 30. The most common symptoms are abdominal pain and bloody diarrhea. The cause of ulcerative colitis is unknown.

Crohn's disease is an inflammatory bowel disease that causes inflammation of the lining of the digestive tract, leading to abdominal pain, severe diarrhea and, in extreme cases, malnutrition. The inflammation can penetrate deep into the tissue. There is no known cure for Crohn's disease, and it is commonly treated with anti-inflammatories and immune system suppressors, for example.

It has been shown in the SCD$^{-/-}$ mice, orally administered SIgA can be used to treat the underlying pruritus, preventing the occurrence of ulcerative dermatitis. Additional populations where prevention of inflammatory disorders is indicated are selective serum IgA-deficient individuals and individuals with allergies, particularly humans with gluten allergies, also called gluten sensitivity. Selective IgA Deficiency is the most common of the primary immunodeficiencies. It is defined as the total absence or severe deficiency of IgA. Blood serum levels for IgA deficient persons are usually found to be 7 mg/dl or less, while serum IgA in normal adults ranges from 90 to 450 mg/dl. The disorder is called "selective" because other serum immunoglobulins, such as IgM and IgG, are present at normal or even increased levels. Recurrent infections, allergies such as asthma and food allergies, and autoimmune diseases are common in selective serum IgA-deficient individuals. Humans with an autoimmune disease are another population for which orally administered SIgA is expected to be beneficial.

The SIgA used in the methods described herein can be isolated and/or pure SIgA. SIgA can be isolated from humans or animals who have been exposed to a variety of antigens. Isolated or pure SIgA can be isolated or purified from the intestinal luminal fluid or the intestinal mucosa of a pig or a cow, sheep, chicken, turkey, horse, or a human (e.g., from a human cadaver or from the intestinal contents of a living human donor).

As used herein, intestinal luminal fluid is the fluid found within the intestinal lumen of an animal. The lumen is the interior cavity of the intestine where digested food passes through and nutrients are absorbed. The composition of intestinal luminal fluid varies depending on the diet, fed/fasted state and the disease state of the organism. Intestinal luminal fluid contains, for example, lipids; proteins including SIgA; bacteria; ions such as sodium, potassium and calcium; and solid undigested materials. SIgA can be purified to about 98% purity from intestinal luminal fluid.

Also as used herein, intestinal mucosa refers to the inner wall (luminal lining) of the intestine. The intestine includes an outer wall called the serosa, middle muscle layers, and an interior called the mucosa.

As used herein, the term "isolated" protein includes protein molecules that are separated from at least a fraction of the other protein or non-protein molecules present in the natural source of the protein. An isolated protein is free of a substantial amount of the cellular material or other contaminating polypeptides from the cell, tissue, or bodily fluid source from which the protein is derived. Isolated SIgA may have a concentration of SIgA twice the concentration in the source material, that is, twice the concentration of SIgA in source intestinal mucosa or luminal fluid. In other embodiments, isolated SIgA has a concentration three, four, five, ten or more-fold compared to the concentration in the source intestinal mucosa.

In one embodiment, secretory IgA is isolated from a source that is intestinal mucosa of a pig or a cow, wherein the concentration of secretory IgA in the isolated secretory IgA is at least twice the concentration in the source material, wherein the source material is dried intestinal mucosa, an aqueous preparation of intestinal mucosa, or a dry preparation of proteins prepared from intestinal mucosa.

In one embodiment, an isolated SIgA preparation is a dry preparation sourced from intestinal mucosa, wherein 5% or more of the proteinaceous material in the isolated SIgA comprises IgA. Without being held to theory, it is believed that there are 5-10 g of SIgA for every 100 g of mucosal protein. In other embodiments, greater than 10, 20, 30, 40, 50, 60, 70, 80, 90 or 95% of the proteinaceous material in the isolated SIgA comprises IgA.

The term pure with reference to SIgA means that SIgA is isolated and that the SIgA components (IgA and secretory components) comprise greater than 75%, specifically greater than 85% and more specifically greater than 95% of the protein in the sample. Pure SIgA can be prepared from intestinal mucosa or intestinal luminal fluid.

In one embodiment, the pure SIgA preparation is pasteurized. Pasteurization is a process of heating a liquid to a specific temperature for a defined length of time and then substantially immediately cooling the liquid. The goal of pasteurization is to reduce the number of viable pathogens in a liquid. Exemplary conditions for pasteurization are 50-100° C. for 5-30 seconds or 120-150° C. for 1-8 seconds, for shelf stable pasteurization. As shown herein, pasteurization of the SIgA isolated from pig intestinal mucosa can be important in the use of the SIgA preparations to increase feed efficiency in chicks.

In one embodiment, the pure SIgA composition has secretory IgA lipopolysaccharide (LPS) binding activity. An indirect ELISA can demonstrate the LPS binding activity. In an indirect ELISA, LPS is coated on a microtiter plate. Either intestinal SIgA or serum IgA (a control) is added at various dilutions to the LPS bound on the microtiter plate. After unbound SIgA is removed by washing, the amount of SIgA that bound to the plate bound LPS is detected using an anti-IgA antibody conjugated to an enzyme like horseradish peroxidase plus substrate.

In one embodiment, the pure, pasteurized SIgA is in the form of a pharmaceutical composition comprising a pharmaceutically acceptable excipient.

In one embodiment, a process for purifying a SIgA composition comprises treating the intestinal luminal fluid of a pig or cow with polyethylene glycol having a molecular weight of 3000 to 30,000, and isolating the precipitated SIgA. In one embodiment, the SIgA is enriched at least two-fold compared to the concentration of SIgA in the intestinal luminal fluid. In another embodiment, the method further comprises resuspending the precipitated SIgA is in a solution of polyethylene glycol having a molecular weight of 3000 to 30,000 to produce re-precipitated SIgA, and isolating the re-precipitated SIgA. Resuspension and precipitation can be repeated until a pure SIgA composition as described herein is produced.

In one embodiment, the precipitated SIgA composition is pasteurized as described above.

Precipitated pure SIgA can be subjected to additional treatments/purification steps, such as filter sterilization, precipitations using ice cold ethanol (lower than 0° C. to dissolve the PEG and leave only the pure protein), desalting. Other procedures for purification such as sodium sulfate precipitations and gamma carrageenan, and size exclusion chromatography.

In one embodiment, pure or isolated SIgA is prepared from the intestinal mucosa of a pig or a cow. In one embodiment, the preparation of pure or isolated SIgA includes lysing the intestinal mucosa, removing debris by centrifugation, for example, and then proteins in the supernatant are sequentially precipitated using various concentrations of polyethylene glycol (3.5-15% w/v) having a molecular weight of 3000 to 30,000, such that the SIgA will be isolated from other proteins in the mucosa preparation.

In another embodiment, SIgA is in the form of the dried intestinal mucosa of a pig, chicken, turkey, sheep, or cow, wherein the intestinal mucosa is not hydrolyzed. In a specific embodiment, the dried intestinal mucosa contains an amount of SIgA effective to increase growth rate and/or improve feed efficiency in an animal. While pig intestinal mucosa has been used previously as a source of amino acids in animal feeds, the intestinal mucosa was hydrolyzed to reduce the constituent proteins to amino acids or stabilized to reduce microbial growth. Reducing the protein to amino acids or even small peptides destroys the bioactivity of SIgA in the mucosa. Stabilizing mucosa using denaturing agents such as acid (e.g., hydrochloric acid or phosphoric acid) or sodium bisulfate can denature the bioactivity of SIgA. The inventors of the present application have unexpectedly discovered that unhydrolyzed and unstabilized, dried pig, chicken, turkey, sheep or cow intestinal mucosa is a useful source of functional SIgA. Unhydrolyzed and unstabilized, dried pig, chicken, turkey, sheep or cow intestinal mucosa, can be used, for example, as a supplement in animal feed compositions. As used herein, the term "unhydrolyzed" means that a preparation has not been treated with enzymes, heat (greater than 90° C.) or chemicals under conditions expected to reduce the constituent proteins to amino acids. As used herein, the term "unstabilized" means that chemical additives have not been used, at concentrations that inhibit SIgA bioactivity, to inhibit microbial growth.

In one embodiment, the dried intestinal mucosa is lyophilized, drum dried, or spray dried.

In one embodiment, SIgA is administered in a food composition. For example, a concentration of greater than 0.1 mg/Kg basal animal or human food is expected to produce beneficial results.

The term "basal food composition" refers to a food composition combinable with additives such as the SIgA compositions described herein. Basal food compositions can be suitable for ingestion by a human or an animal. Exemplary food compositions suitable for ingestion by a human include a nutritionally complete formula, a dairy product, a chilled or shelf stable beverage, a soup, a dietary supplement such as a vitamin, a meal replacement, a nutritional bar, confectionery, or other food composition.

The term "basal animal food composition" refers to an animal food combinable with additives such as the SIgA compositions described herein. Basal animal food compositions may include components such as proteins, grains, flavor compositions, vitamins, minerals, preservatives, and the like. In specific embodiments, the basal animal food composition is for an avian, porcine, bovine, ovine, capra, fish, reptile, mollusk, invertebrate animal, horse, dog, or cat.

In one embodiment, the secretory IgA is in the form of a pure, optionally pasteurized secretory IgA composition isolated from the intestinal luminal fluid of a pig. In a specific embodiment, the pure, pasteurized secretory IgA composition comprises greater than 0.1 mg/Kg basal food composition.

In one embodiment, the basal animal food composition is for a dog or a cat and wherein the animal food composition includes an anti-inflammatory amount of SIgA.

In one embodiment, the SIgA is added to a basal food composition in the form of dried intestinal mucosa from a pig or a cow, wherein the dried intestinal mucosa is unhydrolyzed. In an embodiment, the concentration is 1 mg/Kg to 10 grams/Kg of the dried intestinal mucosa to the basal animal food composition. In a specific embodiment, the basal food composition is for a dog or a cat and wherein the animal food composition has anti-inflammatory efficacy.

Also included herein is a dog or cat food additive comprising an excipient and secretory IgA.

Included herein are pharmaceutical compositions comprising pure, pasteurized SIgA and a pharmaceutically acceptable excipient. As used herein, "pharmaceutical composition" means therapeutically effective amounts of the compound together with a pharmaceutically acceptable excipient, such as diluents, preservatives, solubilizers, emulsifiers, and adjuvants. As used herein "pharmaceutically acceptable excipients" are well known to those skilled in the art.

The invention is further illustrated by the following non-limiting examples.

EXAMPLES

Methods

Mouse Model for Ulcerative Dermatitis

Ulcerative dermatitis affects laboratory mice with a C57BL/6J (B6) background, causing excoriation of the face, ears or dorsal cervicothoracic skin, accompanied by pruritus. SCD1$^{-/-}$ mice, lacking stearoyl Co-A denaturase-1, have decreased expression of genes encoding enzymes used to synthesize lipids and increased expression of genes encoding enzymes that oxidize fatty acids. It has been shown (Krugner-Higby et al., Ulcerative Dermatitis in C57BL/6 Mice lacking Stearoyl CoA Desaturase I, Comparative Medicine, 62, pp. 257-263 (2012)) that SCD1$^{-/-}$ mice fed a semipurified diet based on NIH AIN76A develop skin ulcers and can be used as a model of ulcerative dermatitis. Semipurified diets are derived from single-source components so that the lipid, protein or carbohydrate source can be changed by varying a single component.

The NIH AIN76A diet includes corn oil as the lipid source, casein as the protein source, and sucrose and corn starch as the major carbohydrate sources. The AIN76A composition is given in Table 1:

TABLE 1

Composition of NIH AIN76A diet

| Component | g/kg |
| --- | --- |
| Casein | 200.0 |
| DL-methionine | 3.0 |
| Sucrose | 499.99 |
| Corn starch | 150.0 |
| Corn oil | 50.0 |
| Cellulose | 50.0 |
| Mineral mix, AIN-76 | 35.0 |
| Vitamin mix, AIN-76A | 10.0 |
| Choline bitartrate | 2.0 |
| Ethoxyquin (antioxidant) | 0.01 |

Control mice are wild type mice with functioning SCD that, when switched to the AIN diet, rarely develop UD.

As reported in Krugner-Higby, all SCD1$^{-/-}$ mice on the NIH AIN76A diet spontaneously develop skin lesions within 4 weeks of initiation of the NIH AIN76A diet, while few or no wild-type mice fed the AIN diet develop skin lesions. Ulcerative dermatitis includes ulceration over the neck or dorsum, with crusting, scabbing or oozing. The mice were also pruritic, with self-trauma and occasional lameness.

Preparation of Crude Swine Intestinal Mucosa

Mucosa is homogenized with up to 50% (of total volume) water to dilute the material and encourage cell lysis. Mucosa can then be filtered using an 800 μm filter and/or centrifuged at 4000×g for 10 minutes. Mucosa is homogenized using a standard two-stage dairy homogenizer at a final pressure of 2000 psi. Mucosa is pasteurized at 160° F. for 20 seconds. Mucosa is spray dried at 2000 psi and 350° F. in a standard spray dryer (4-stories in height). Material is tested for activity using ELISA(s) (described below).

Preparation of Purified Swine Intestinal IgA

Luminal fluid from commercially slaughtered pigs was collected. Luminal fluid was combined with 3.5% PEG 8000 w/v (polyethylene glycol 6000-8000 molecular weight) and centrifuged at 14,000×g, 4° C. for 10 minutes. The clarified liquid was collected and filtered through glass wool to remove any remaining fats. The clarified liquid was combined with 8.5% PEG 8000 w/v and centrifuged at 14,000× g, 4° C. for 10 minutes. The supernatant was poured off and the pellet within the tube was resuspended in 12% PEG 8000 w/v in deionized water. The mixture was centrifuged at 14,000×g, 4° C. for 10 minutes. The supernatant was poured off and the remaining pellet was frozen at −80° C. and then lyophilized.

The purity of the pellet and activity of the mucosa was determined by ELISA. Briefly, 96 well plates were coated with goat anti-pig IgA antibody (120 uL) from Bethyl Laboratories (Montgomery Tex.) dissolved in coating buffer (1.59 g Na$_2$CO$_3$, 2.93 g NaHCO$_3$, 0.2 g NaN$_3$, pH 9.6, 1000 mL total volume) overnight to allow for attachment of the antibody to the Nunc Maxisorp® F plate (Thermo-Fisher Scientific, Rochester N.Y.). Plates were blocked with protein free blocking buffer (Pierce, Rockford Ill.) for 1 hour. Plates were washed 3 times with PBS-0.05% Tween (Fisher-Scientific, Pittsburgh Pa.). Samples were added to the plate in 10-fold dilutions from 1:10-1:1,000,000,000 for 1 hour to determine the amount of IgA present. Pig reference serum was provided as a control. Plates were washed 3 times with PBS-0.05% Tween. Goat anti-porcine IgA secondary antibody (Bethyl Laboratories, Montgomery Tex.) was added in blocking buffer (5 μL 2° antibody:12.5 mL blocking buffer) for 30 minutes. The plates were washed 6 times with washing buffer. Substrate was added in substrate buffer (diethanolamine 97 mL, 100 mg $MgCl_2$, 0.2 g $NaN_3$, 800 mL $ddH_2O$, pH 9.8), incubated for 15 minutes, and read at 450 nm.

IgA purity: Luminal fluid (fluid collected from within the intestinal tract through a series of rollers that express intestinal contents without disruption of the mucosal lining) demonstrated greater than 90% purity after purification. There was between 193 and 199 mg of IgA/200 mg of total product.

Pasteurization was used to eliminate live bacteria from the IgA preparations. A commercial grade pasteurizer from the University of Wisconsin-Madison Dairy Pilot Plant heated the luminal fluid containing IgA to 160° F. for 20 seconds, and the material was cooled quickly there-after. There was almost no loss in the amount of IgA and no decrease in the antigen-binding activity of the IgA after pasteurization.

Example 1

Developing a Capture Murine sIgA for the Purpose of Quantifying Mouse Intestinal Lumen sIgA: Specificity of Anti-Murine IgA Antibodies Briefly, murine IgA was purchased from (Bethyl Laboratories, Montgomery Tex.) and was emulsified with Freund's complete adjuvant and injected into laying hens. Hens were given one week to recover from the vaccination. Commercial murine IgA was emulsified with Freund's incomplete adjuvant and injected into the same laying hens seven days later. Hens were monitored for anti-murine IgA production. Once production was verified using an ELISA, anti-murine IgA egg antibodies were purified using the same PEG procedure as was used for purifying swine SIgA. Anti-murine IgA antibodies were then conjugated to horseradish peroxidase (HRP). 3 mg of the purified anti-murine SIgA antibody was combined with 3 mg of HRP (Sigma®) and then 40 μL of 1% glutaraldehyde was added for 3 hours. The reaction was stopped by adding 20 mg of glycine and incubating for one hour at 21° C. The mixture was dialyzed overnight against PBS (phosphate buffered saline).

The specificity of the anti-murine SIgA antibodies was tested using an ELISA. Murine IgA was dissolved in coating buffer (1.59 g $Na_2CO_3$, 2.93 g $NaHCO_3$, 0.2 g $NaN_3$, pH 9.6, 1000 mL total volume), and pipetted into Nunc Maxisorp® F plates (Thermo-Fisher Scientific, Rochester N.Y.) overnight to allow for attachment of the murine IgA to the plates. The plates were blocked with protein free blocking buffer (Pierce, Rockford Ill.) for 1 hour. The plates were washed three times with PBS-0.05% Tween (Fisher-Scientific, Pittsburgh Pa.). Plates were then tested using one of three treatments: 1) HRP-labeled anti-murine IgA egg antibodies (HRP), 2) HRP-labeled and unlabeled anti-murine IgA egg antibodies (HRP with competition), and 3) control or non-specific egg antibodies and HRP-labeled anti-murine IgA egg antibodies (HRP with control antibody). The three antibody treatments were added to the plates in 10-fold dilutions from 1:10-1:1,000,000,000 to determine the amount of murine IgA present. The plates were incubated at 21° C. for 1 hour. The plates were then washed three times with PBS-0.05% Tween. Plates were washed 6 times with washing buffer. HRP-substrate (hydrogen peroxide) was added in substrate buffer (diethanolamine 97 mL, 100 mg $MgCl_2$, 0.2 g $NaN_3$, 800 mL $ddH_2O$, pH 9.8), incubated for 15 minutes, and the plates were read at 450 nm. As shown in FIG. 1, there was significantly more binding to murine IgA measured for the HRP-conjugated anti-murine IgA egg antibody (group 1) and HRP-conjugated anti-murine IgA egg antibody plus control non specific egg antibody groups (group 3) than with the HRP-conjugated and unconjugated anti-murine IgA egg antibody (group 2). This result demonstrates that the anti-murine IgA egg antibody binds the murine IgA substrate and can be out-competed with an unlabeled anti-murine IgA egg antibody, but not with a control nonspecific egg antibody. The anti-murine IgA egg antibody that was made is specific for the substrate of murine IgA and can be used in a capture ELISA to quantify mouse luminal sIgA (see Example 2).

Example 2

Figure 2:
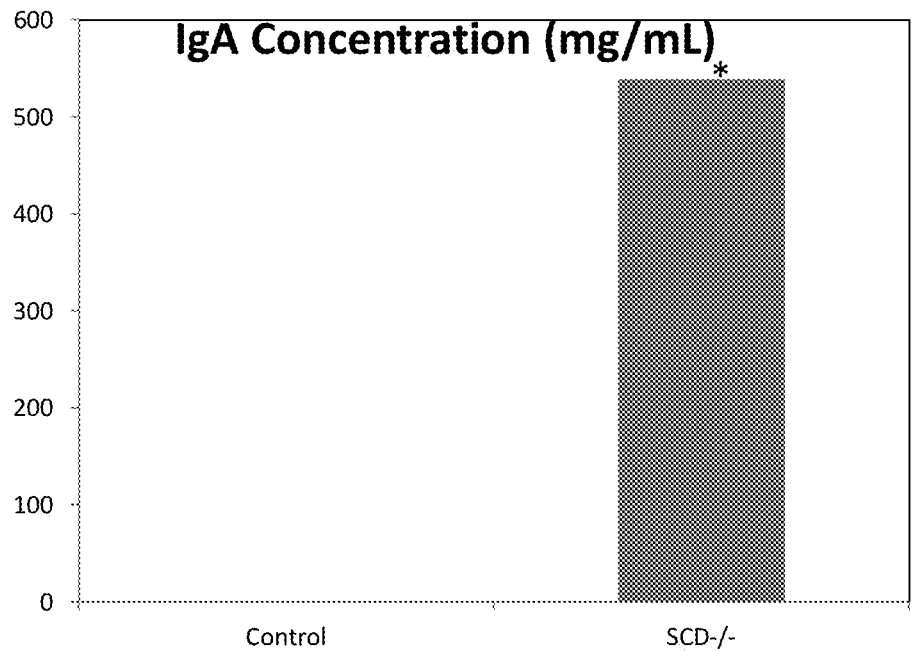
FIG. 2 shows the base luminal secretory IgA in control and $SCD1^{-/-}$ mice quantified using an ELISA involving the anti-murine IgA egg antibodies described in FIG. 1. There is a statistically significant increase in the amount of luminal IgA in the $SCD1^{-/-}$ mice. * $P<0.07$.

Baseline Luminal Secretory IgA in Control and $SCD1^{-/-}$ Mice $SCD1^{-/-}$ and control C57BL/6 mice were examined for the secretory IgA content of their luminal fluid. In each group, three mice were euthanized and the luminal fluid was extracted. A capture ELISA was used to detect murine IgA in the extracted luminal fluid. Unlabeled anti-murine IgA egg antibody from Example 1 was dissolved in coating buffer (1.59 g $Na_2CO_3$, 2.93 g $NaHCO_3$, 0.2 g $NaN_3$, pH 9.6, 1000 mL total volume) overnight to allow for attachment of the antibody to the Nunc Maxisorp® F plate (Thermo-Fisher Scientific, Rochester N.Y.). The plates were blocked with protein free blocking buffer (Pierce, Rockford Ill.) for 1 hour. The plates were washed three times with PBS-0.05% Tween (Fisher-Scientific, Pittsburgh Pa.). Luminal fluid samples from six different mice (3 $SCD1^{-/-}$ and 3 control) were added to the plate in 10-fold dilutions from 1:10-1:1,000,000,000 to determine the amount of IgA present. The plates were incubated at 21° C. for 1 hour. The plates were washed 3 times with PBS-0.05% Tween. Chicken anti-murine IgA egg antibody labeled with HRP was added in blocking buffer (5 μL 2° antibody:12.5 mL blocking buffer) for 60 minutes. The plates were washed 6 times with washing buffer. Substrate was then added in substrate buffer (diethanolamine 97 mL, 100 mg $MgCl_2$, 0.2 g $NaN_3$, 800 mL $ddH_2O$, pH 9.8), incubated for 15 minutes, and the plates were read at 450 nm. As shown in FIG. 2, the baseline luminal secretory IgA in the $SCD1^{-/-}$ mice was 500× greater than in the control mice.

Given the higher concentration of secretory IgA in the $SCD1^{-/-}$ mice, it would not be expected that adding additional secretory IgA would have a significant effect on ulcerative dermatitis in mice fed the NIH AIN76A diet. However, without being held to theory, it is also possible that the $SCD1^{-/-}$ mice have an over-reaction to the change in diet, resulting in the increase in secretory IgA.

In addition, histology of the intestines of the ulcerative dermatitis model mice shows an increase in inflammation and decreased submucosal and muscular thickness in the duodenum (data not shown). Without being held to theory, it is believed that the increased IgA in the intestines of the mice with ulcerative dermatitis is due to the increased secretory IgA in the intestines.

Example 3

Evaluation of Oral Administration of Crude Swine Intestinal Mucosa as an Ulcerative Dermatitis Prevention and Treatment Without being held to theory, it is believed that antigens (e.g., dietary, microbial or casein) initiate the ulcerative dermatitis response in the SCD1$^{-/-}$ mice on the NIH AIN76A diet Six mice were used in the control group and in the test group fed crude swine intestinal mucosa. In the control group there were five mice with no evidence of ulcerative dermatitis, and one control mouse with ulcerative dermatitis. In the test group, there were five mice with no evidence of ulcerative dermatitis, and one mouse with ulcerative dermatitis. Control mice were fed the NIH AIN76A diet supplemented with acidified PBS (phosphate-buffered saline) and test mice were fed the NIH AIN76A diet supplemented with 1 g/kg crude swine oral mucosa in acidified PBS. The mice were monitored daily and weighed weekly.

Table 2 shows the effects of orally administered crude swine intestinal mucosa in the prevention and treatment of ulcerative dermatitis.

TABLE 2

Effect of crude swine intestinal mucosa on ulcerative dermatitis

| Time | Treatment | Number of mice with ulcerative dermatitis |
|---|---|---|
| Start of treatment- mice with ulcerative dermatitis (1 per group) | Control diet | 1/1 |
| | Test diet | 1/1 |
| After one month of treatment/mice with ulcerative dermatitis (1 per group) | Control diet | Severe ulcerative dermatitis by visual inspection of lesions. |
| | Test diet | Significant improvement in ulcerative lesions by visual inspection. |
| After one month of treatment/mice with no evidence of ulcerative dermatitis (5 per group) | Control diet | 4/5 |
| | Test diet | 2/5 |

As can be seen from Table 2, the mouse with ulcerative dermatitis that was fed the control diet deteriorated greatly during the 4 week study. The mouse with ulcerative dermatitis fed the test diet improved greatly during the 4 week study. This result suggests that crude swine intestinal mucosa can reverse ulcerative dermatitis in the mouse model.

As can further be seen from Table 2, of the mice without ulcerative dermatitis at the beginning of the 4 week study, 4/5 mice on the control diet developed ulcerative dermatitis, compared with 2/5 mice on the test diet. Thus, crude swine intestinal mucosa can prevent ulcerative dermatitis in the mouse model.

Ulcerative dermatitis was also quantitatively determined using the following scoring system:
1. Less than 10% of the skin is open (raw) with no deep or open sores.
2. Less than 20% of the skin is open (raw) with one or less open sores, or if there is more than 20% raw skin with no open sores.
3. Less than 30% of the skin is raw, with 2 or less open sores.
4. Less than 40% of the skin is raw with 3 or less open sores; animals are euthanized if they stay at this level.

Figure 3:
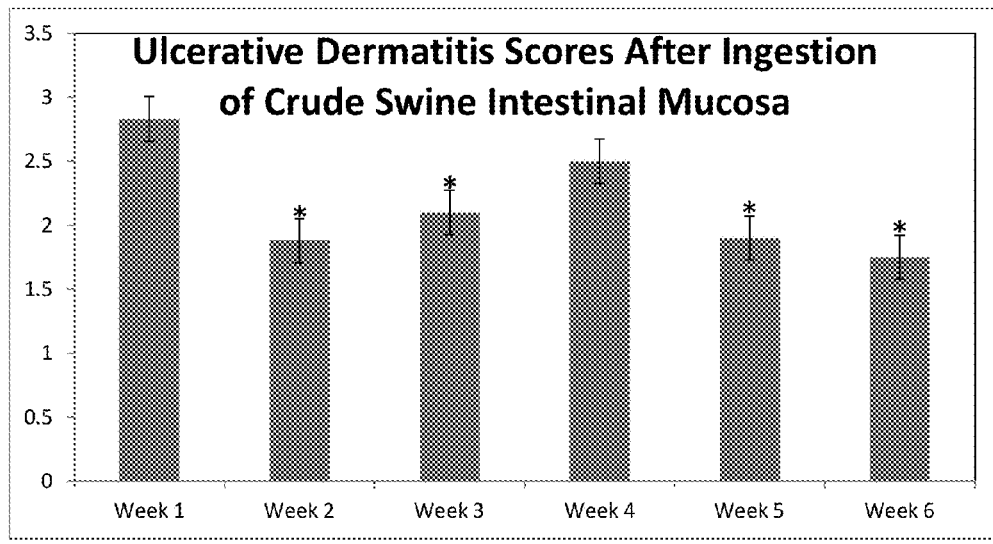
FIG. 3 shows ulcerative dermatitis (UD) scores for $SCD^{-/-}$ mice fed a semipurified casein-based diet supplemented with crude swine intestinal mucosa containing SIgA. The reported numbers are an average of the weekly total UD score/number of days/the number of animals. There is a significant decrease in UD scores from week one to week six in the mice consuming crude swine intestinal mucosa. *=$P<0.05$.

As shown in FIG. 3, SCD1$^{-/-}$ mice with ulcerative dermatitis consuming crude swine intestinal mucosa were monitored daily for UD score. The presented data is an average of the weekly total UD score/number of days/the number of animals. There is a significant decrease in UD score with the mice consuming crude swine intestinal mucosa. *=P<0.05

Figure 4:
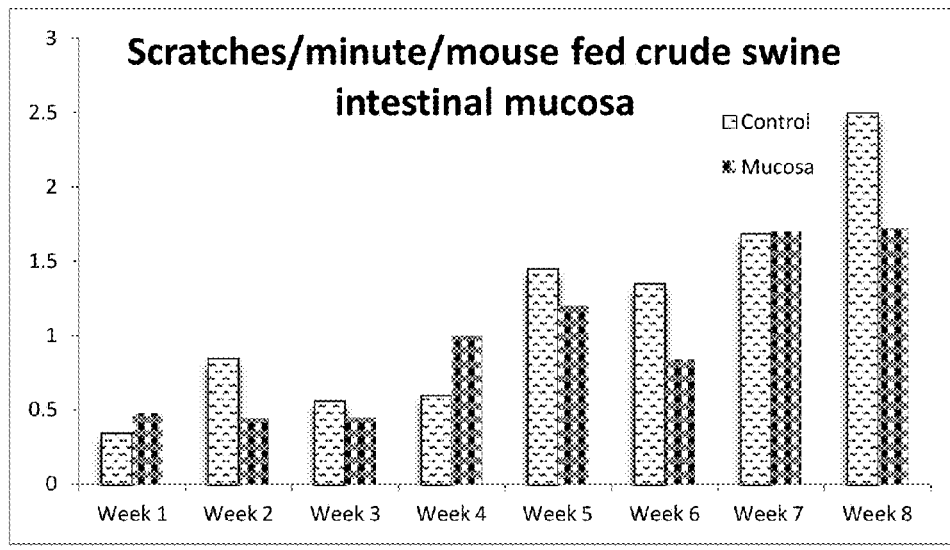
FIG. 4 shows scratching data for the control animals and $SCD^{-/-}$ mice fed a semipurified casein-based diet supplemented with crude swine intestinal mucosa. The presented data are an average of the weekly total number of scratches/the number of days/the number of animals. There is no significant difference between the control or crude swine intestinal mucosa.

Scratching was also quantitated in the control mice and the mice fed crude swine intestinal mucosa. SCD1$^{-/-}$ mice consuming either control (no addition of mucosa material) or crude swine intestinal mucosa were monitored daily for scratching. Each mouse was observed for one minute to determine if they were scratching and how many times during that one minute time frame they did scratch. The reported data is an average of the weekly total number of scratches/the number of days/the number of animals. As shown in FIG. 4, while there was no significant difference between the control animals and the animals fed crude swine intestinal mucosa the first 7 weeks, mice fed mucosa appeared to have less scratching (approximately 30% less) than the controls on week 8.

Example 4

Determination of Active Component in Crude Swine Intestinal Mucosa

It was hypothesized that the active component in the crude swine intestinal mucosa is secretory IgA. To test this hypothesis, mice were treated with purified swine intestinal secretory IgA. 28 SCD1$^{-/-}$ mice were fed either an NIH AIN76A diet supplemented with 1 g/Kg swine secretory IgA or 0.33 g/Kg swine secretory IgA (Control from previous work with 100% incidence of dermatitis=8 mice; SIgA at 0.33 g/Kg=14 mice; SIgA at 1 g/Kg=14 mice). The incidence of ulcerative dermatitis was monitored for 12 weeks. The data is shown in Table 3:

TABLE 3

Effect of Purified Swine IgA on Ulcerative Dermatitis in Mouse Model

| Treatment | Mice with Ulcerative Dermatitis | % Incidence |
|---|---|---|
| Control (from Krugner-Higby) | 8/8 | 100 |
| 0.33 g/kg** | 7/14 | 50 |
| 1 g/kg | 2/14 | 14 |

**Bioactivity was reduced to ⅓ activity after heating to 80° C. for 30 minutes using *E. coli*: 55 LPS and isolated soy protein in an ELISA.

The data in Table 3 confirms that the active component in crude swine intestinal mucosa is secretory IgA.

Example 5

Treatment of Ulcerative Dermatitis with Purified Swine Secretory IgA

Four mice with ulcerative dermatitis (SCD1$^{-/-}$ mice fed the NIH AIN76A diet) were fed the NIH AIN76A diet supplemented with 1 g/kg diet purified swine secretory IgA.

Figure 5:
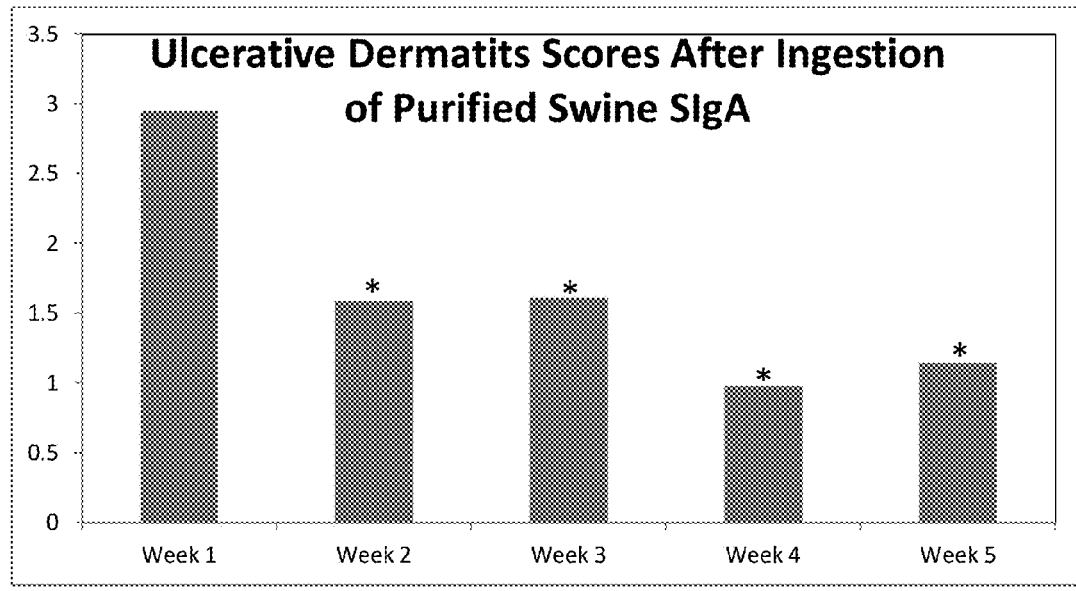
FIG. 5 shows UD scores for $SCD^{-/-}$ mice fed a semipurified casein-based diet supplemented with purified swine secretory IgA. The reported numbers are an average of the weekly total UD score/number of days/the number of animals. There is a significant decrease in UD score with the mice consuming purified swine SIgA. *=$P<0.001$.

As shown in FIG. 5, SCD1$^{-/-}$ mice with ulcerative dermatitis consuming purified swine SIgA were monitored daily for UD score. The presented data is an average of the weekly total UD score/number of days/the number of animals. There is a significant decrease in UD score with the mice consuming crude swine intestinal mucosa. *=P<0.001. In all four cases, the severity of the ulcerative dermatitis was reduced. Thus, purified swine secretory IgA reverses ulcerative dermatitis in the mouse model.

Figure 6:
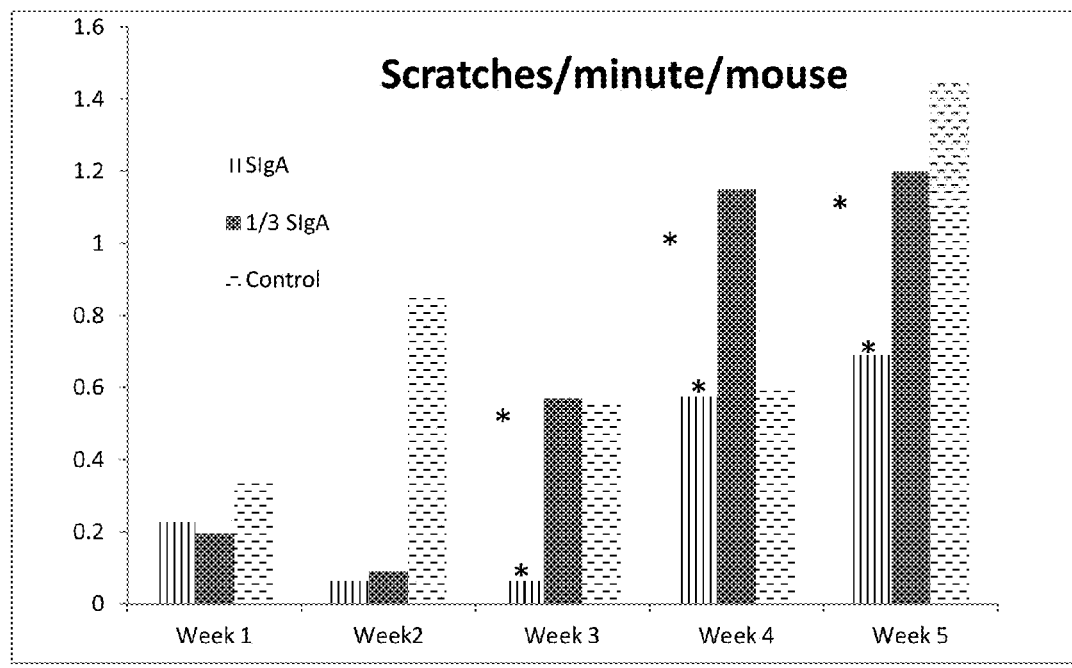
FIG. 6 shows scratching data for the control animals and $SCD^{-/-}$ mice fed a semipurified casein-based diet supplemented with purified swine secretory IgA. There is a significant decrease in scratching with the mice consuming purified swine secretory IgA. *=$P<0.03$ The above-described and other features will be appreciated and understood by those skilled in the art from the following detailed description, drawings, and appended claims.

As further evidence that SIgA reduces ulcerative dermatitis, scratching was determined in control mice and the mice fed purified swine SIgA. SCD1$^{-/-}$ mice consuming either control with no added SIgA, ⅓ activity purified swine SIgA (0.33 gram of SIgA/Kg) or full activity purified swine SIgA (1 gram of SIgA/Kg) and were monitored daily for scratching. Each mouse was observed for one minute to determine if they were scratching and how many times during that one minute period the mouse scratched. The reported data is an average of the weekly total number of scratches/the number of days/the number of animals. (FIG. 6) There is a significant decrease in scratching with the mice consuming purified swine SIgA. *=P<0.03

It has been shown herein, using the SCD$^{-/-}$ mouse model of dermatitis, that orally administered swine intestinal mucosa or purified swine SIgA resulted in a dose-dependent reduction in the development of ulcerative dermatitis. In addition, in mice with ulcerative dermatitis, orally administered swine intestinal mucosa or purified swine SIgA dramatically reduced or eliminated the symptoms of ulcerative dermatitis in all four of the treated mice that had ulcerative dermatitis. The methods described herein are particularly useful to treat inflammation of barrier surface structures, including ulcerative dermatitis and gastrointestinal disorders.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of for treating inflammation in a barrier surface structure in a mammal in need thereof, comprising orally administering to the mammal an anti-inflammatory amount of secretory IgA, wherein the secretory IgA is isolated from the intestinal luminal fluid or the intestinal mucosa of an animal.

2. The method of claim 1, wherein the mammal is a human or a non-human mammal.

3. The method of claim 1, wherein the inflammation is in a barrier surface structure associated with dermatitis.

4. The method of claim 3, wherein the dermatitis is atopic dermatitis, chronic actinic dermatitis, ulcerative dermatitis, allergic contact dermatitis, or irritant contact dermatitis.

5. The method of claim 4, wherein the mammal is an infant diagnosed with infantile eczema.

6. The method of claim 4, wherein the mammal is a dog diagnosed with atopic dermatitis.

7. The method of claim 6, wherein the dog has hot spots.

8. The method of claim 7, wherein the dog is prednisone-intolerant, wherein prednisone is contraindicated due to side effects, or wherein the dog is co-administered a medication that is incompatible with steroid administration.

9. The method of claim 4, wherein the dermatitis is ulcerative dermatitis.

10. The method of claim 9, wherein the mammal is a C57BL/6 background laboratory mouse.

11. The method of claim 9, wherein the mammal is a cat with feline ulcerative dermatitis, or a pig with porcine ulcerative dermatitis.

12. The method of claim 4, wherein the mammal suffers from skin lesions that are resistant to healing.

13. The method of claim 1, wherein the inflammation in a barrier surface structure is associated with an inflammatory disorder that includes chronic gastrointestinal inflammation.

14. The method of claim 13, wherein inflammatory disorder that includes chronic gastrointestinal inflammation is inflammatory bowel disease, ulcerative colitis, Crohn's disease, lymphocytic or eosinophilic gastroenteritis.

15. The method of claim 14, wherein the chronic inflammatory disorder is inflammatory bowel disease and the mammal is a dog, a cat or a farmed animal.

16. The method of claim 13, wherein the mammal is a human suffering from ulcerative colitis or Crohn's disease.

17. The method of claim 1, wherein the mammal is selective serum IgA-deficient, and orally administering IgA prevents or reduces the development of inflammatory disorders characterized by inflammation of a barrier surface structure in the mammal.

18. The method of claim 1, wherein the mammal has allergies, and orally administering IgA reduces the development of inflammatory disorders characterized by inflammation of a barrier surface structure in the mammal.

19. The method of claim 18, wherein the mammal is a human with a gluten allergy.

20. The method of claim 1, wherein the mammal is a human with an autoimmune disease.

21. The method of claim 1, wherein the secretory IgA is isolated from the intestinal luminal fluid or the intestinal mucosa of a pig or a cow.

22. The method of claim 1, wherein the intestinal mucosa of an animal is stabilized and unhydrolyzed.

* * * * *